United States Patent [19]

Ito et al.

[11] 3,966,913

[45] June 29, 1976

[54] ANTIBIOTICS NO. K-73 AND METHOD FOR PRODUCING THE SAME

[75] Inventors: Akiro Ito, Saitama; Yasushi Ichikawa, Fuji; Sadayuki Horiguchi, Fuji; Shyoji Shirota, Fuji; Yasuo Kayama; Shiro Chihara, both of Tokyo; Isoko Haneda, Yamato; Katsumi Hasuda, Niiza; Shyoichi Takano, Hanno, all of Japan

[73] Assignee: Kayaku Antibiotic Research Co., Ltd., Tokyo, Japan

[22] Filed: Jan. 23, 1975

[21] Appl. No.: 543,500

[52] U.S. Cl. ............................ 424/119; 195/80 R
[51] Int. Cl.$^2$ ..................................... A61K 35/74
[58] Field of Search ..................... 424/119; 195/80

[56] References Cited
OTHER PUBLICATIONS

Miller, The Pfizer Handbook of Microbial Metabolites, McGraw–Hill Book Co., Inc., N.Y., N.Y., 1961, pp. 266 & 267.

*Primary Examiner*—Jerome D. Goldberg
*Attorney, Agent, or Firm*—Oblon, Fisher, Spivak, McClelland & Maier

[57] ABSTRACT

An antibiotic designated as No. K-73A, which is produced by cultivating a strain of *Streptomyces tanashiensis* K-73, and then isolating and recovering the antibiotic from the cultured broth thereof.

5 Claims, 2 Drawing Figures

ANTIBIOTICS NO. K-73 AND METHOD FOR PRODUCING THE SAME

BACKGROUND OF THE INVENTION

This invention relates generally to a new class of antibiotics and a method for producing them. More particularly, this invention pertains to the new and useful antibiotic designated as No. K-73A, and methods for producing it from the cultural broth of a newly isolated organism, *Streptomyces tanashiensis* K-73.

As a result of a continuous program of research for the production of new and useful antibiotics a new strain of bacteria which produces a new class of antibiotics has been isolated from a soil sample collected in Tokyo, Japan. This bacterial strain has been deposited with the Antibiotic Industrial Techniques Laboratory, of the Japanese Academy of Industrial Techniques, and has been given Acceptance No. 2399. This bacterial strain has also been deposited with the American Type Culture Collection in the United States, and has been given ATCC Acceptance No. 31,053.

SUMMARY OF THE INVENTION

One object of this invention is to provide a new antibiotic designated as No. K-73A.

Another object of this invention is to provide a method for producing antibiotic designated as No. K-73A.

A further object of this invention is to provide methods of separating an antibiotic designated as No. K-73A from a crude complex of antibiotics designated as No. K-73.

Briefly, these objects and other objects of this invention as hereinafter will become readily apparent can be attained by a process for producing antibiotic K-73A which comprises culturing a strain of *Streptomyces tanashiensis* K-73, and then isolating and recovering said antibiotic K-73A from said cultured broth.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
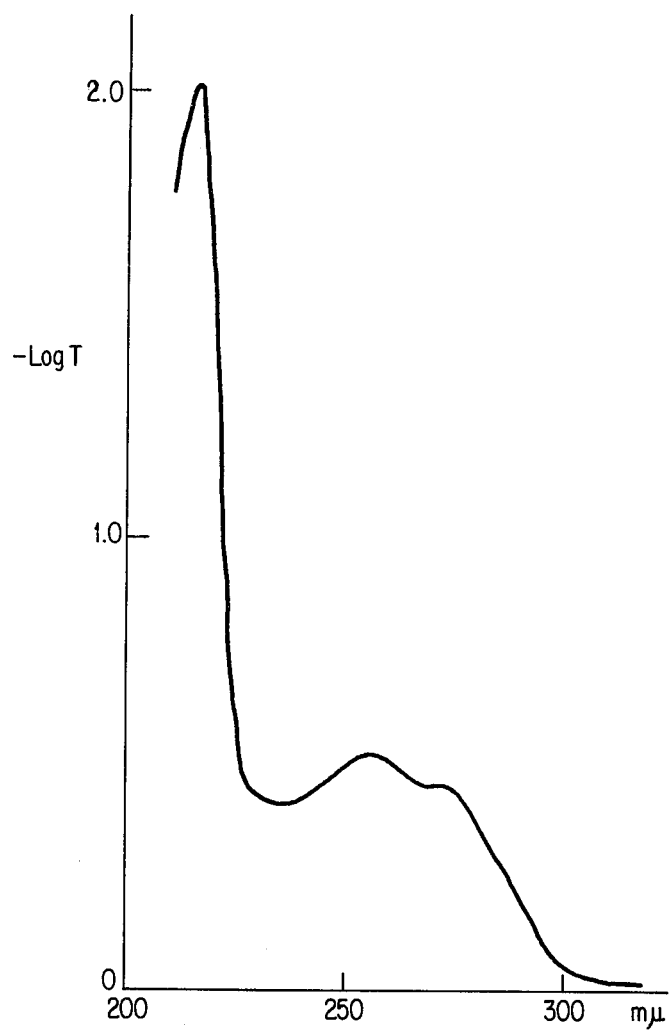
FIG. 1 is the ultraviolet absorption spectrum of antibiotic No. K-73A hydrochloride.

Bacteriological characteristics of *Streptomyces tanashiensis* K-73.

MORPHOLOGICAL CHARACTERISTICS

According to microscopic and electron microscopic observations of this bacterial strain grown in organic and synthetic media, aerial mycelia are straight or loosely curved, the spore is cylindrical of 0.5 to 0.6 × 0.9 to 1.1 $\mu$ in size, and it forms an approximately linear spore chain. The spore surface is smooth.

GROWTH CHARACTERISTICS OF THE BACTERIA IN VARIOUS MEDIA

1. Sucrose-Czapek's Agar (27°C.):
Growth of the bacteria is poor and colorless, aerial mycelia are white, and soluble pigment is not produced.

2. Glucose Asparagine Agar (27°C.):
Bacterial growth is grayish yellow, with gray aerial mycelia. Soluble pigment is faint brown.

3. Calcium malate Agar (27°C.):
Growth of the bacteria is moderate and yellow, and aerial mycelia are white. Soluble pigment is reddish brown.

4. Peptone Nitrate Solution (27°C.):
A pellicle is formed on the surface of solution and flocks are formed on the bottom. Gray aerial mycelia cover the full surface, and soluble pigment is pale brown.

5. Bouillon Agar (27°C.):
Substrate growth is pale brown and glistening, and aerial mycelia is scant and, soluble pigment is pale grayish brown.

6. Glucose Nutrient Agar (27°C.):
Substrate growth is wrinkled and brownish color. Aerial mycelia are thin, light gray. Soluble pigment is brown.

7. Röffler's Serum (37°C.):
Substrate growth is grayish-brown with no aerial mycelia. Soluble pigment is deep brown, and serum is hydrolyzed.

8. Potato Plug (27°C.):
Substrate growth is wrinkled, black to brownish yellow. The aerial mycelia are light brownish-gray, and soluble pigment is brown.

9. Gelatin medium (24°C.):
Growth is ring and brown. The aerial mycelia are brownish-white, and a deep brown soluble pigment is produced. The gelatin is liquefied.

10. Starch Agar (27°C.):
Substrate growth is white, and aerial mycelia are gray. Soluble pigment is pale brown. Starch is strongly hydrolyzed.

11. Milk (27°C.):
Growth is ring, and the aerial mycelia are none. Brown soluble pigment is produced.

12. Cellulose-Czapek's Agar (27°C.):
Substrate growth is poor and white. Aerial mycelia are scant. No soluble pigment is produced.

13. Bennett's Agar (27°C.):
Substrate growth is good and brown. Aerial mycelia are brownish gray, and soluble pigment is deep brown.

14. Tyrosine Agar:
The bacteria grow moderately well, and the aerial mycelia are gray. Tyrosinase is produced and the medium becomes dark brown.

15. Glucose-Czapek's solution:
The bacterial growth is moderate and flocks are produced on the bottom. Surface growth is not observed and soluble pigment is not produced.

16. Yeast extract-Malt extract Agar
Substrate growth is good. Aerial mycelia are brownish gray and soluble pigment is dark brown.

17. Oatmeal Agar
Substrate growth is poor and flat. Aerial mycelia are brownish gray. Soluble pigment is yellowish.

18. Glycerin-Asparagine Agar
Substrate growth is moderate. Aerial mycelia are gray. Soluble pigment is yellow.

PHYSIOLOGICAL PROPERTIES

This bacteria is aerobe growing over the range of pH 4.5 to 8.0 and possible to grow over the range of 10° to 40°C.

| | | |
|---|---|---|
| 2. | Liquefication of Gelatin: | Positive |
| 3. | Hydrolysis of Starch: | Positive |
| 4. | Peptonization of Milk: | Positive |
| 5. | Nitrate Reduction: | Positive |
| 6. | Cellulose Decomposition: | Positive |
| 7. | Formation of Melanin: | Positive |
| 8. | Coagulation of Milk: | Negative |
| 9. | Casein Decomposition: | Positive |
| 10. | Formation of Tyrosinase: | Positive |

Utilization of carbon sources of this bacteria is shown in Table 1 as tested by Pridham & Gottlieb's method.

TABLE 1

| | | | | | |
|---|---|---|---|---|---|
| Glucose | ++ | Galactose | + | Maltose | + |
| Glycerol | ++ | Xylose | + | Fructose | ± |
| Inositol | − | Arabinose | + | Sodium Citrate | − |
| Mannitol | − | Raffinose | − | | |
| Rhamnose | − | Sucrose | − | | |

CODE:
++Good utilization
+ moderate utilization
− none utilization

When the bacterial strain is checked with Bergly's Manual of Determinative Bacteriology (7th edition) and confirmed, it is evident that the strain belongs to *Streptomyces* by the following reason. That is, it grows well under aerobic condition at an optimum temperature range of from 25° to 35°C. The bacteria consists of substrate mycelia which have no septa and aerial mycelia adhering of liuba spore chains formed cylindrical spores. The strain resembles *Streptomyces tanashiensis*. However, it is differentiated from *S. tanashiensis* in the following respects:

a. This strain form white aerial mycelia on Sucrose-Czapek's Agare, but *S. tanashiensis* forms no aerial mycelia.
b. This strain produces faint brown soluble pigment in Glucose Asparagine Agar, but *S. tanashiensis* does not produce pigment.
c. This strain forms light gray aerial mycelia in Glucose Nutrient Agar, but *S. tanashiensis* forms white aerial mycelia.
d. This strain forms brownish-gray aerial mycelia on Potato Plug, but *S. tanashiensis* forms brownish-white aerial mycelia.
e. This strain produces deep brown soluble pigment in Bennett's Agar, but *S. tanashiensis* produces pale brown soluble pigment.
f. This strain forms brownish gray aerial mycelia and produces deep brown soluble pigment in Yeast extract-Malt extract Agar, but *S. tanashiensis* forms gray aerial mycelia and produces pale brown soluble pigment.
g. This strain produces faint yellow soluble pigment in Oatmeal Agar, but *S. tanashiensis* does not produce soluble pigment.
h. This strain produces yellow soluble pigment on Glycerin Asparagin Agar, but *S. tanashiensis* does not produce soluble pigment.

As mentioned above, there are lesser difference between the subject strain and *S. tanashiensis*. Therefore, the strain is designated as *Streptomyces tanashiensis* K-73.

In order to obtain the antibiotic No. K-73 complex, *Streptomyces tanashiensis* K-73 is inoculated in a nutrient-containing medium and is aerobically cultured.

Suitable nutrients include nitrogen sources such as soybean meal, peptone, meat extract, corn steep liquor, cotton seed lees, peanut lees, malt extract, yeast extract, nitrates, ammonium salts, and the like; carbon sources such as glucose, glycerin, galactose, xylose, maltose, starch and the like; inorganic salts such as chlorides, nitrates, phosphate and sulfates of alkali metals and alkaline earth metals such as magnesium, zinc and manganese.

Cultivation of the bacteria is preferably conducted at temperatures from 25°–30°C and pH 5.5 to 8, and industrially superior result is obtained by submerged culture under aerobic condition. After cultivation for 24–96 hours, production of the antibiotic No. K-73 complex will reach a maximum.

In order to extract the antibiotic No. K-73 complex from the culture broth, the broth is filtered at neutral, or acidic pH by the addition of an inorganic acid such as hydrochloric acid or sulfuric acid; or an organic acid such as oxalic acid, acetic acid or the like. If required, the broth can be heated, and then the cells are separated by filtration. Thereafter, the filtrate is extracted with a water insoluble organic solvent. Suitable organic solvents include chloroform, ethyl acetate, butyl acetate, benzene, butanol, ether and the like.

Although the antibiotic No. K-73 is contained in the bacterial cells, it can be extracted the antibiotic from the cells, with hydrophilic solvents such as methanol, ethanol, acetone and the like, or aqueous mixtures of these solvents.

In order to isolate the antibiotic No. K-73 from the enormous volumes of cultured liquid used in industrial scale operation, active adsorbents or precipitators can also be used in addition to the said extraction methods. Suitable adsorbents include active carbon, kaolin, synthetic adsorbents and the like. Suitable precipitators include picric acid, helianthine B and the like.

The antibiotic No. K-73 obtained above is a mixture of two or more components, which can be separated by conventional chemical refining methods such as chromatography, precipitation, solvent extraction or any suitable combination of the separation techniques into antibiotics No. K-73A and others.

The antibiotics No. K-73 and No. K-73A are new materials, and antibiotic No. K-73A hydrochloride has the following physico-chemical properties and antimicrobial spectrum.

A. PHYSICO-CHEMICAL PROPERTIES

Figure 2:
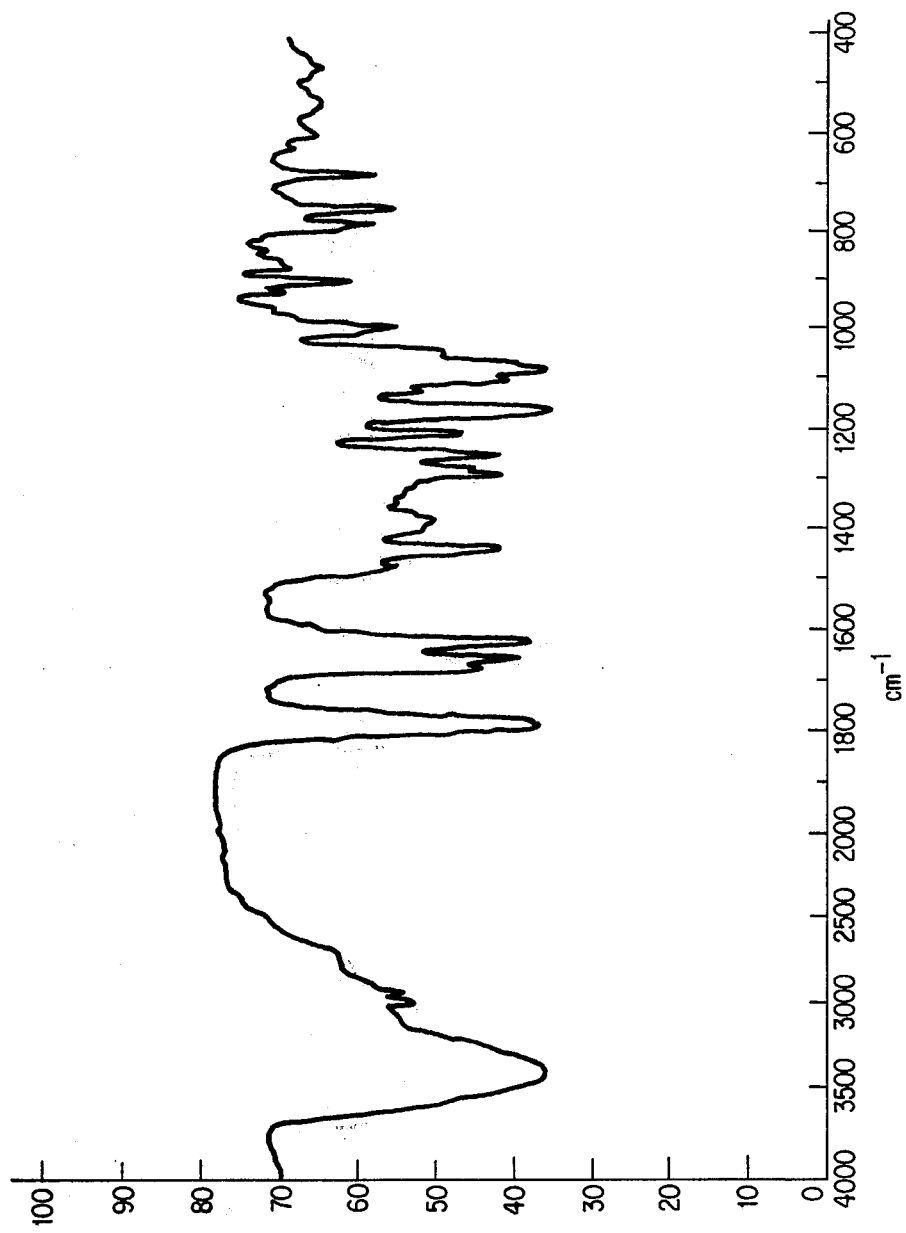
FIG. 2 is the infrared absorption spectrum of antibiotic No. K-73A hydrochloride.

1. Specific rotation: $[\alpha]_D^{25} + 177°C$ (C = 2, chloroform)
2. Molecular weight: 496
3. Chemical formula: $C_{24}H_{29}NO_8 \cdot HCl$
4. Elemental analysis (%): C 57.73, H 6.39, N 2.35.
5. Melting point: 180°C (decomposition)
6. Ultraviolet absorption spectrum: FIG. 1
7. Infrared absorption spectrum: FIG. 2
8. Solubility
   Soluble in water, methanol, ethanol, acetone, ethyl acetate and benzene. Insoluble in n-hexane and petroleum ether.
9. Color reaction:

Baeyer, anthron, Fehling and quinone reactions are positive. Ninhydrin, biuret and Elson-Morgan reactions are negative.

10. Nature:
Basic substance (pKa = 9.5)

B. ANTIBIOTIC ACTIVITY

TABLE 2

| Test organisms | Minimum inhibitory concentration (mcg/ml) |
| --- | --- |
| Staphylococcus aureus 209P | 0.2 |
| Staphylococcus aureus FS3271 | 0.8 |
| Staphylococcus aureus FS3839 | 0.4 |
| Staphylococcus aureus FS3891 | 0.4 |
| Staphylococcus aureus FS3904 | 0.2 |
| Staphylococcus aureus FS3877 | 0.4 |
| Staphylococcus epidermidis IFO3762 | 0.4 |
| Sarcina lutea PCI1001 | 0.4 |
| Bacillus subtilis PCI219 | 0.4 |
| Bacillus cereus IFO3001 | 0.4 |
| Escherichia coli NIHJ | 100.0 |
| Escherichia coli K12 | 50 |
| Aerobacter aerogenes IAM1063 | 100 |
| Serratia marcescens IAM1022 | 100 |
| Proteus vulgaris IFO3045 | 50 |
| Proteus morganii IFO3848 | 50 |
| Proteus mirabilis IFO3849 | 100 |
| Proteus rettgeri | 100 |
| Pseudomonas aeruginosa IFO3901 | 100 |
| Shigella flexneri 2a | 12 |
| Salmonella infantis | 50 |
| Salmonella enteritidis | 100 |
| Xanthomonas oryzae IAM1657 | 6 |

(Note)
FS 3271: Resistant bacteria of TC.CP.SM.
FS 3839: Resistant Bacteria of TC.SM.SP.
FS 3877: Resistant bacteria of TC.CP.KM.SP.EM.-LeuM. OM.LM.
FS 3891: Resistant bacteria of TC.KM.SP.EM.OM.LM.
FS 3904: Resistant bacteria of TC.CP.KM.SP.EM.

C. Acute toxicity (mice)

$LD_{50}$: 8.8 mg/Kg (intravenous injection)
620 mg/Kg (oral administration)

Antibiotic No. K-73A of the present invention has also particularly excellent therapeutic effect on coccidiosis.

Chickens of white leghorn immediately after incubation were bred while they were prevented from infection with coccidia. Chickens aged 9 days were so divided into the groups consisting of 10 animals respectively, that each of which was nearly equal in the body weight. Of these, two groups were taken as an infected control and a no-infected control.

To the test group was given the assorted feed for new born chickens to which was added 0.005 to 0.01 % by weight of antibiotic No. K-73A. The assorted feed for new born chickens containing no drugs was given to the control.

After 24 hours from feeding, $5 \times 10^4$ oocysts of *Eimeria tenella* were given to each chickens of the test groups exclusive of no-infected control group. On fifth to seventh days after administration the rate of the increase in body-weight and the bloody excrements of chickens were observed. Chickens were submitted to dissection on seventh day, and the lesion of the caecum was inspected.

The results obtained are as shown in the following table.

|  |  | Increase in body-weight | | | State of bleeding | | | Lesion of caecum | | | | |
| --- | --- | --- | --- | --- | --- | --- | --- | --- | --- | --- | --- | --- |
|  |  | Mean body-weight at start of testing (g) | Rate of increase in body-weight | Ratio of rates of increase in body-weight | 5 days after | 6 days after | 7 days after | − | + | ++ | +++ | ++++ |
| Test group | Added 0.005% of Antibiotic No. K-73A | 58.5 | 1.45 | 1.04 | no | no | no |  | 6/10 | 4/10 |  |  |
|  | Added 0.01% of Antibiotic No. K-73A | 58.2 | 1.48 | 1.06 | no | no | no | 8/10 | 2/10 |  |  |  |
| Control group | Infected control | 59.0 | 1.04 | 0.75 | much | much | little |  |  |  | 2/10 | 8/10 |
|  | No-infected control | 58.6 | 1.39 | 1.0 | no | no | no | 10/10 |  |  |  |  |

(Notes)
The rate of the increase in body-weight:
  Mean body-weight at the end of testing
  Mean body-weight at the start of testing
The ratio of the rates of the increase in body-weight:
  The ratio of the rate of increase to that of no-infected group.
The state of bleeding:
  The amount of bleeding from the intestines of chickens are expressed as the numbers of shots of blood.
The lesion of caecum:
  −normal, +slight, ++slight but a little lesion is observed.
  +++moderate, hypertrophy is observed. ++++severe, lesion is very clearly observed.

Accordingly, in order to prevent coccidiomycosis in animals, 0.05 to 0.1 % by weight of antibiotic No. K-73A is preferably added to the feed.

The antibiotic No. K-73A may be administered to animal in form of powder, tablets, granules, capsules, or liquid form as solutions, suspensions or emulsions. And also the antibiotic No. K-73A may be administered to animal in admixture with carrier, such as feed or an ingredient of feed. The carrier includes soybean meal, alfalfa meal, cotton seed oil meal, linseed oil meal, cornmeal, cane molasses, bone meal, corncob meal, and the like.

Having generally described this invention, a further understanding can be obtained by reference to certain specific examples which are provided herein for purpose of illustration only and are not intended to be limiting unless otherwise specified.

EXAMPLE 1

A culture medium of pH 7.0 was prepared containing 3 % starch, 1 % peptone, 1 % meat extract, 0.5 % sodium chloride and 0.2 % calcium carbonate.

Seed of *Streptomyces tanashiensis* K-73 grown at 27°C for 24 hours in the same medium, was inoculated in the above culture medium and cultivated with stirring at 30°C for 40 hours with aeration. A 2 Kg amount of celite was added to 200 l of the cultured broth, and the culture broth was filtered and separated into a cellular mass and a filtrate. The filtrate was passed through a column containing about 10 l of Amberlite XAD-II (Trade name of Rome & Haas Co.). After washing the column with 10 times volume of water, the active material adsorbed was eluted with 70 % aqueous acetone to yield 15 l of an active fraction. The eluate was concentrated to 5 l under reduced pressure, and the concentrate was adjusted to pH 7.5 and extracted three times with equal volumes of chloroform.

The chloroform layer was extracted with one-half volume of an dil. hydrochloric acid solution, and the water layer was concentrated under reduced pressure and then lyophilized to yield 9 g of the orange yellow antibiotic No. K-73 complex.

EXAMPLE 2

200 l of cultured broth filtrate prepared by the same procedure as in Example 1 was adjusted to pH 7.5 with N- sodium hydroxide, and 80 l of ethyl acetate was added thereto, and then the mixture was stirred for 1 hour. After the resulting mixture was allowed to stand, ethyl acetate layer was collected, and concentrated to 10 l by Flash-evaporater. The concentrate was extracted 5 times with 1 l of hydrochloric acid solution of pH 1.0, and acidic aqueous layer was adjusted to pH 5.0 and then lyophilized to yield 10 g of the antibiotic No. K-73 complex.

EXAMPLE 3

1 g of the antibiotic No. K-73 complex obtained as in Examples 1 and 2 was dissolved in 100 ml of n-butanol with heating, and insoluble matter was filtered off. The n-butanol solution was allowed to stand in cooled place to obtain 500 mg of crude crystals. The crude crystals were recrystallized with acetone-metanol to obtain 300 mg of orange colored cryslates of antibiotic No. K-73A.

EXAMPLE 4

A 1 g amount of the antibiotic No. K-73 complex obtained as in Example 1 was passed through a phosphonomethyl cellulose column which had been previously buffered with 0.02M acetate buffer (pH 4.0), and then 0.02M acetate buffer (pH 5.0) was passed through the column. At first, antibiotic No. K-73B was eluted, and thereafter antibiotic No. K-73A was eluted. 250 ml of the fraction containing the antibiotic No. K-73A was collected and extracted with chloroform at pH 7.5. The antibiotic was reextracted with small volume of dil acidic water, and thereafter the water layer was lyophilized at pH 5.0 *t* yield 250 mg of light orange powder of antibiotic No. K-73A.

Having now fully described this invention, it will be apparent to one of ordinary skill in the art that many changes and modifications can be made thereto without departing from the spirit or scope of the invention as set forth herein.

What is claimed is:

1. A process for producing an antibiotic designated as No. K-73 complex containing antibiotic No. K-73 A which comprises cultivating a strain of Streptomyces tanashiensis K-73, ATCC No. 31,053, in a culture medium including nitrogen sources, carbon sources and inorganic salts at 25°–30°C and PH 5.5–8 under aerobic conditions for 24–96 hours to accumulate the antibiotics, isolating and recovering said antibiotic No. K-73 complex from the cultured broth.

2. A process according to claim 1, wherein said cultivation is conducted at a temperature of 25° to 30°C in a submerged culture under aerobic conditions.

3. A method for recovering antibiotic No. K-73A from antibiotic No. K-73 complex produced in accordance with claim 1 which comprises preparing antibiotic No. K-73 complex in accordance with claim 1, dissolving the complex in heated n-butanol and recovering the crystals obtained on cooling the n-butanol solution.

4. Antibiotic No. K-73A hydrochloride which is described by the following characteristic properties:
   1. Specific rotation: $[\alpha]_D^{25} + 177°$ (C=2, chloroform)
   2. Molecular weight: 496
   3. Chemical formula: $C_{24}H_{29}NO_8 \cdot HCl$
   4. Elemental analysis (%): C 57.73, H 6.39, N 2.35
   5. Melting point: 180°C (decomposition)
   6. Ultraviolet absorption spectrum: FIG. 1
   7. Infrared absorption spectrum: FIG. 2
   8. Solubility:
      Soluble in water, methanol, ethanol, acetone, ethyl acetate and benzene. Insoluble in n-hexane and petrolem;
   9. Color reaction:
      Balyer, Anthron, Fehling and Quinone reactions are positive; Ninhydrin, Biuret and Elson-Margan reactions are negative;
   10. Nature
       Basic substance (pKa=9.5).

5. An anticoccidium composition comprising 0.05 to 0.1 % by weight of an antibiotic No. K-73A in feed.

* * * * *